(12) United States Patent
Shoura et al.

(10) Patent No.: US 12,091,660 B2
(45) Date of Patent: Sep. 17, 2024

(54) DETECTION AND ANALYSIS OF STRUCTURAL VARIATIONS IN GENOMES

(71) Applicants: The Board of Trustees of the Leland Stanford Junior University, Stanford, CA (US); BOARD OF REGENTS, THE UNIVERSITY OF TEXAS SYSTEM, Austin, TX (US)

(72) Inventors: Massa Shoura, Stanford, CA (US); Andrew Z. Fire, Stanford, CA (US); Stephen Levene, Richardson, TX (US)

(73) Assignees: The Board of Trustees of the Leland Stanford Junior University, Stanford, CA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 18/298,202

(22) Filed: Apr. 10, 2023

(65) Prior Publication Data
US 2023/0287397 A1    Sep. 14, 2023

Related U.S. Application Data

(63) Continuation of application No. PCT/US2021/055078, filed on Oct. 14, 2021.

(60) Provisional application No. 63/092,315, filed on Oct. 15, 2020.

(51) Int. Cl.
*C12N 15/10* (2006.01)

(52) U.S. Cl.
CPC ............... *C12N 15/1065* (2013.01)

(58) Field of Classification Search
CPC .................................... C12N 15/1065

USPC ............................................. 506/4
See application file for complete search history.

(56) References Cited

U.S. PATENT DOCUMENTS

2015/0072869 A1 * 3/2015 Vilfan ............. C12Q 1/6844
506/26

FOREIGN PATENT DOCUMENTS

| WO | WO2016130704 | 8/2016 | |
| WO | WO2017151828 | 9/2017 | |
| WO | WO-2019157529 A1 * | 8/2019 | ....... C07K 14/70539 |

OTHER PUBLICATIONS

RecBCD. Wikipedia. 6 pages, revision date Sep. 29, 2019 by user "BrownHairedGirl". [Retrieved on Aug. 23, 2023]. Retrieved from Internet: <URL:https://en.wikipedia.org/w/index.php?title=RecBCD &oldid=918615533> (Year: 2019).*

(Continued)

*Primary Examiner* — Aaron A Priest
*Assistant Examiner* — Randi Lynn Beil
(74) *Attorney, Agent, or Firm* — Pamela J. Sherwood; Bozicevic, Field & Francis LLP

(57) ABSTRACT

Compositions and methods are provided for detection of dynamic loci in a genome, where such loci may comprise structural variations as a result of DNA recombination; DNA duplication, insertions, deletions, transpositions, and epigenetic changes. The methods may utilize microfluidic platforms and functionalized polymer matrices to allow determination of mechanisms of cell-type-specific, programmed genomic heterogeneity. The method and compositions allow determination of mechanisms of cell-type-specific, programmed genomic heterogeneity.

20 Claims, 4 Drawing Sheets
Specification includes a Sequence Listing.

(56) References Cited

OTHER PUBLICATIONS

Chen et al. Nucleic acid modifications in regulation of gene expression. Cell Chemical Biology. 23, 2016, 74-85. (Year: 2016).*
Rajala, N et al. (2015) "Whole Cell Formaldehyde Cross-Linking Simplifies Purification of Mitochondrial Nucleoids and Associated Proteins Involved in Mitochondrial Gene Expression." PLOS One. Feb. 19, 2015, vol. 10, No. 2, e0116726; pp. 1-20.

* cited by examiner

FIG. 3A
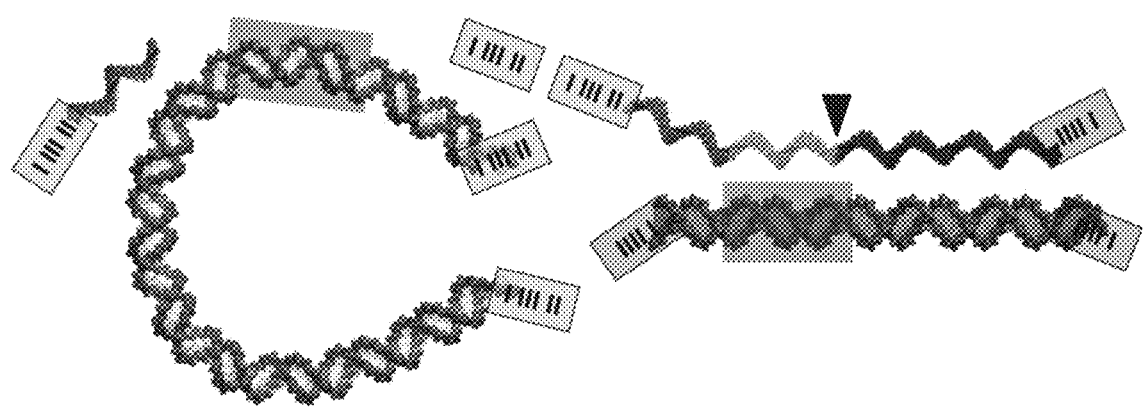
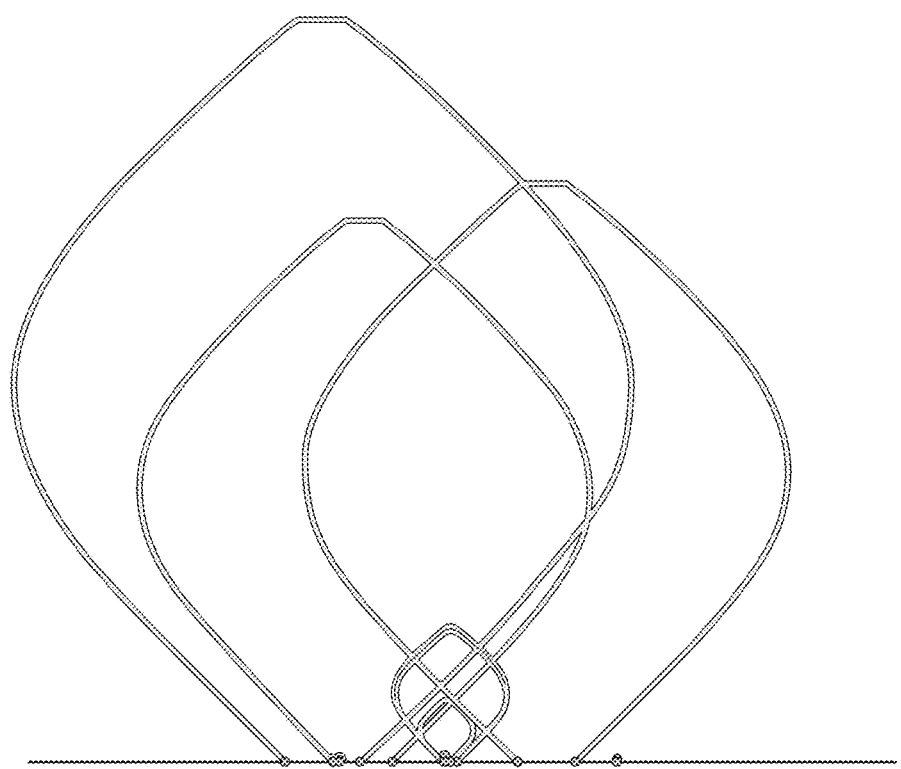
FIG. 3B

DETECTION AND ANALYSIS OF STRUCTURAL VARIATIONS IN GENOMES

CROSS REFERENCE TO RELATED APPLICATION

This application is a Continuation and claims the benefit of PCT Application No. PCT/US2021/055078, filed Oct. 14, 2021, which claims benefit of U.S. Provisional Patent Application No. 63/092,315, filed Oct. 15, 2020, which applications are incorporated herein by reference in their entirety.

GOVERNMENT SUPPORT SPONSORSHIP

This invention was made with Government support under contract GM130366 awarded by the National Institutes of Health. The Government has certain rights in the invention.

INCORPORATION BY REFERENCE OF SEQUENCE LISTING

A Sequence Listing is provided herewith as a Sequence Listing XML, S19-447_STAN-1798CON Sequence Listing, created on Dec. 11, 2023, and having a size of 73,602,528 bytes. The contents of the Sequence Listing XML are incorporated herein by reference in their entirety.

BACKGROUND

Genomes are not static. They are dynamic and modify their content, context, and architecture in response to intrinsic and extrinsic signals. These genomic rearrangements and epigenetic changes result in altered phenotypes that have consequences for cellular development, programmed biological function, and disease. Elements of heterogeneous sequence and/or structure contribute to functional dynamics and somatic mosaicism. Informatic and technical limitations have hindered investigations of these elements, leading to ambiguities that obscure intercellular genomic nonuniformity. Moreover, defining the mechanisms responsible for heterogeneity will require new, higher-resolution approaches that can capture, characterize, and catalog bona fide variants of all types (insertions, deletions, SNPs, CNVs, epigenetic changes, etc.)

As one important example of such changes, extrachromosomal-circular DNAs (eccDNA, microDNA, double minute chromosomes, or ecDNA), a distinct topological form of DNA, are emerging as a potential biomarker for genomic variation, immune adaptation and function, cancer, and other diseases. A major challenge in characterizing such structural variation in detail has been the challenge of examining the consequences of individual genome structures for specific cells and for groups of cells, particularly at complex and biomedically significant loci having partial redundancy and potential cell-to-cell variability at the level of DNA sequence or of gene function.

The present disclosure provides methods for the generation of single cells embedded in a functionalized polymer matrix for detection and analysis of bona fide structural and functional variations in genomes and genome activity at the resolution of single cells or groups of cells.

SUMMARY

Compositions and methods are provided for detection of dynamic loci in a genome, where such loci may comprise structural variations as a result of DNA recombination; DNA duplication, insertions, deletions, transpositions, and epigenetic changes. The genomic nucleic acid may be obtained from cells, e.g. intact cells, extracellular vesicles (EVs), etc. Such methods facilitate detailed characterization of heterogeneous genomic elements, e.g. repetitive DNAs and extrachromasomal circular DNAs, etc. The methods may utilize microfluidic platforms and functionalized polymer matrices. The method and compositions allow determination of mechanisms of cell-type-specific, programmed genomic heterogeneity.

In some embodiments, methods are provided for the generation of one or more cells or EVs embedded in a functional polymer matrix, herein termed "pearls", for the detection and analysis of structural variations at genomic loci. Target cells, EVs, biological samples, etc. for analysis may be isolated, for example, from a subject of interest from a suitable biological sample, wherein the subject is an individual suspected to be suffering from a condition associated with DNA rearrangements, including but not limited to: cancer, immune modulation, changes to immune memory and/or immune function; and the like. In some embodiments, target cells or EVs are sorted, for example using techniques, including but not limited to: flow cytometry, fluorescent activated cell sorting, magnetic activated cell sorting, microfluidics, etc.

In some embodiments a microfluidics device is used to generate single cells or EVs embedded in a functional polymer matrix, i.e. pearls. In some embodiments, single cells are directly injected into pre-formed polymer pearls. The polymer matrix is selected to allow for: buffer exchange; permeability to large molecules including, for example, enzymes and proteins; entrapment of nucleic acids inside the matrix during lysis; and stability over a range of temperatures, including without limitation from about −4° C. to about 65° C. In some embodiments the polymer matrix comprises, without limitation, agarose, hydrogel, or Pluronic polymers at a concentration sufficient to inhibit degradation of DNA by mechanical shearing. In some embodiments the embedded cells are lysed in situ, and the matrix is then dissolved in a chaotropic dense salt solution. The matrix is dissolved by the chaotropic salt at ambient temperature, e.g. from about 10° to about 40° C.

In some embodiments, polymer pearls are made using a microfluidics platform. In such embodiments, cells, oil (e.g. mineral oil) and polymer can be mixed in a microfluidic chamber to form pearls comprising a single cell. Pearls provide a benefit of allowing processing of cells while keeping nucleic acids trapped within the matrix. "Pearls" find use in analyses requiring intact genomes, intact high-molecular weight library preparation or for the isolation and processing of DNA or RNA.

In some embodiments, the polymer pearls comprising one or more cells are washed to remove oils and any other unwanted compounds or contaminants prior to buffer exchange for lysis. The methods may use further processing steps, including but not limited to, exonuclease treatment to digest linear DNA. The pearls may be dissolved using a salt solution to free the nucleic acids.

In some embodiments, chromatinized DNA is fixed to proteins before dissolving the pearls. In some embodiments, non-destructive labeling of genomic DNA is performed prior to analysis using DNA barcodes, fluorophores, or other unique molecular identifiers via crosslinking reagents such as psoralen conjugates. In some embodiments, crosslinkers are targeted to specific genomic sequences through drug, nucleic-acid, or other moieties that recognize specifically targeted genomic sequences, or alternatively that are sequence non-specific. In some embodiments, crosslinking is chemically or physically reversible to avoid interference with subsequent processing for sequencing pipelines. In some embodiments, after lysis, DNA is digested and the remaining RNA is isolated, modified, reverse PCR'ed, or sub-isolated based on structure, sequence, size, or native modifications. In some embodiments, after lysis, nucleic acid polymers are fragmented. In some embodiments, during fragmentation barcodes are inserted. In some embodiments, during fragmentation primers comprising barcodes and sequencing platform adapters are added to the fragmented nucleic acids using a transposase. In some embodiments the bar-coded nucleic acids are used to generate a library.

Custom primers may be utilized, where the primers comprise one or more chemical modifications that increase the melting temperature of the duplex formed between the target DNA and the primer. The modifications may include, without limitation, inclusion of modified nucleotides such as Pyrene, Trimethoxystilbene, 2-Amino-deoxyadenosine, 5-Methyl-deoxycytidine, LNA, BNA, Aminoethyl-phenoxazine-deoxycytidine, C-5 Propynyl-deoxyuridine, C-5 Propynyl-deoxycytidine, MGB, etc. Adding modifications can increase sequencing efficiency, allowing the generated libraries to be sequenced by a sequencing platform of interest. In some embodiments, sequencing efficiency and quality are increase by at least 10% using primer modifications. In some embodiments, sequencing efficiency is increased from 10-20%, 20-30%, 30-40%, 40-50% or >50% using primer modifications.

BRIEF DESCRIPTION OF THE DRAWINGS

FIGS. 3A-FIG. 3B. FIG. 3A. CNN-Seq barcoding detection. Incorporated barcodes are sequenced from both top and bottom strands via paired-end sequencing. Unmatched barcodes due to PCR artifacts are detected bioinformatically using a pipeline we developed. Reads that bear deletion, insertion, or circular junctions without matching barcodes are marked. Confidence score is assigned to each junctional read based on incidence supported by unique reads. FIG. 3B: Confirmed deletion junctions in cardiomyocytes are plotted after CNN-seq was performed. Analysis confirmed 97% of observed junctions.

DETAILED DESCRIPTION

Definitions

Figure 1A:
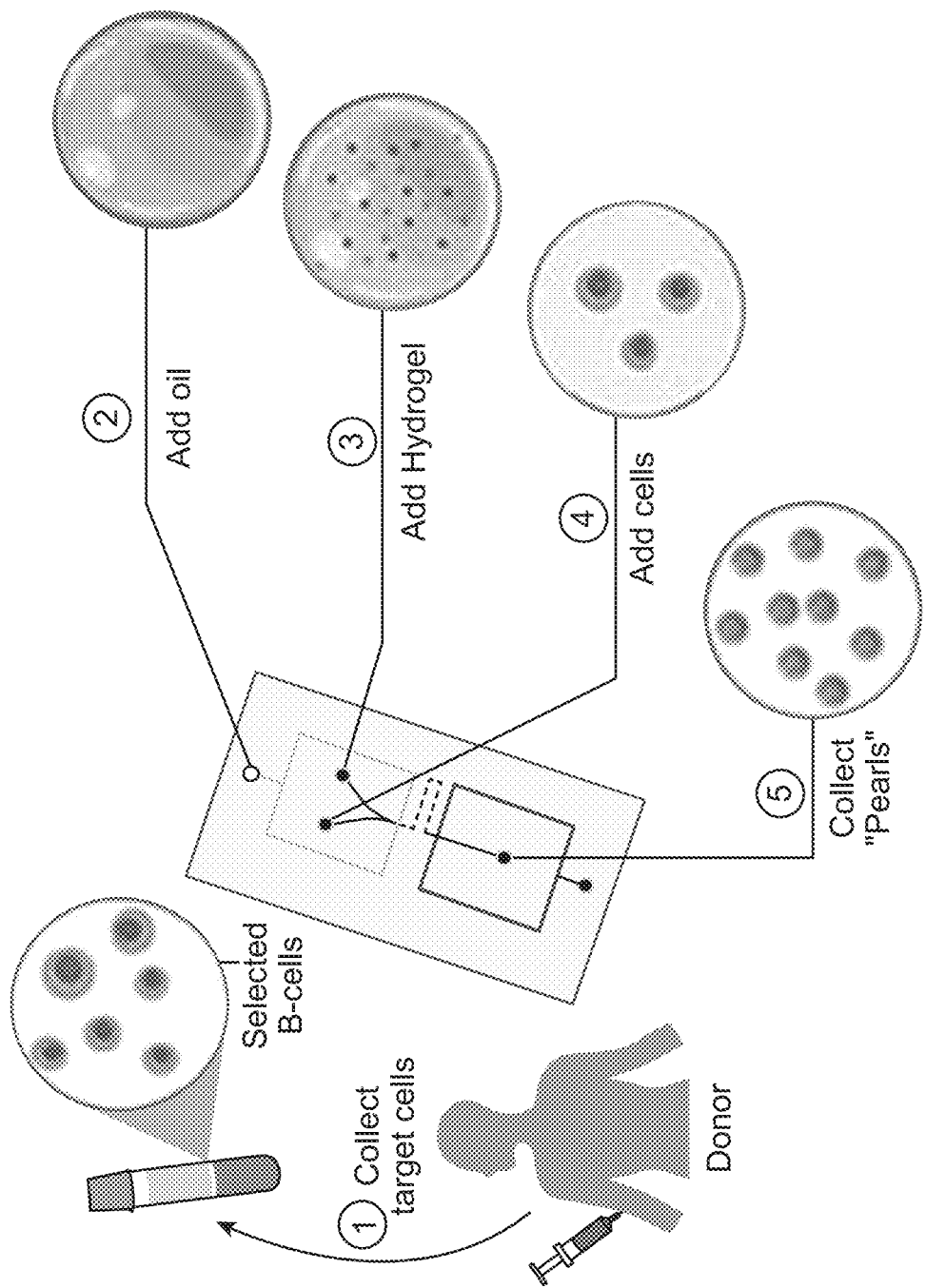
FIGS. 1A-1B. A workflow of "Boba-seq". A. One method of generating single cells that are embedded in a functionalized polymer matrix is through a simple microfluidics platform. The resulting single-cell "pearls" are then washed and subjected to a quick buffer exchange and lysis. B. Barcoded libraries of genomic DNA (or circular DNA after treatment with ExoV, an exonuclease that digests linear DNA only), can be obtained by digesting DNA with the use of a transposase. DNA can be released pre- or post-PCR, using a patented solution that is capable of dissolving the polymer matrix at room temperature without any damage to the DNA (or RNA).
Figure 1B:
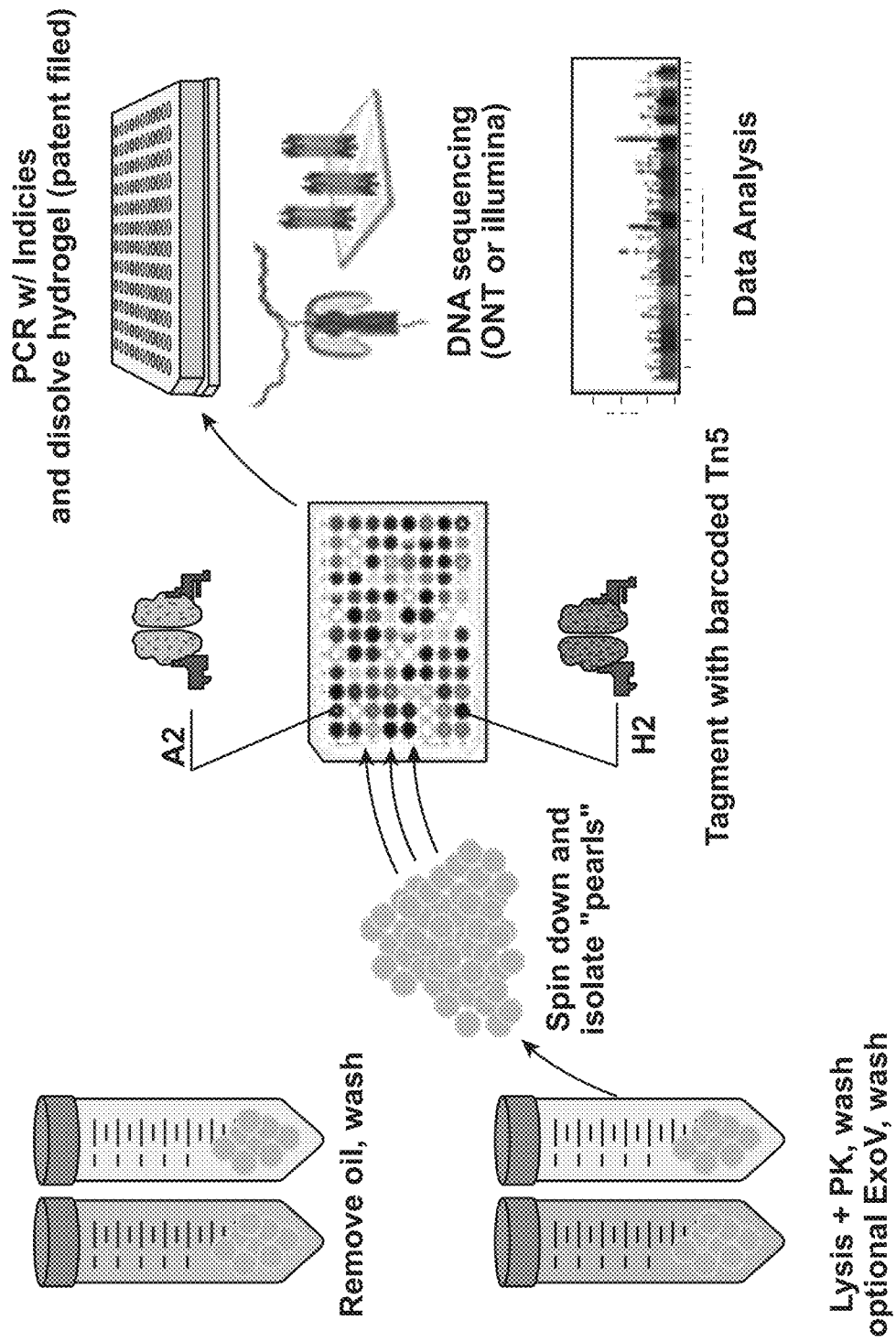

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease (e.g., reduction in viral titers).

The terms "individual," "host," "subject," and "patient" are used interchangeably herein, and refer to an animal, including, but not limited to, human and non-human primates, including simians and humans; rodents, including rats and mice; bovines; equines; ovines; felines; canines; avians, and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the term "structural variation" refers to physical or chemical variation within a nucleic acid sequence in a genome. Structural variations may include, but are not limited to, nucleic acid sequence deletions, duplications, copy-number variants, insertions, inversions, translocations, fusions, rearrangements, long-term repeats, short-term repeats, and epigenetic variants at the level of DNA modification, alterations in histone modification, and alterations in physical configuration of the genome.

Matrix and polymers. In some embodiments the matrix single cells are embedded in, include without limitation, a natural or synthetic hydrogel. Various polymers find use for this purpose, with the general requirement that the polymer matrix structure can be formed around cells under physiologically acceptable conditions and will be dissolved in the chaotropic salt solution at ambient temperatures.

Some examples of biodegradable polymers useful in the present invention include: hydroxyaliphatic carboxylic acids, either homo- or copolymers, such as polylactic acid, polyglycolic acid, polylactic glycolic acid; polysaccharides such as cellulose or cellulose derivatives such as ethyl or methyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthalate and calcium alginate, polypropylene, polybutyrates, polycarbonate, acrylate polymers such as polymethacrylates, polyanhydrides, polyvalerates, polycaprolactones such as poly-epsilon-caprolactone, polydimethylsiloxane, polyamides, polyvinylpyrollidone, polyvinylalcohol phthalate, gelatin, agarose, starch, alginate, reversibly cross-linked hydrogels, elastin polypeptides, hyaluronan, PEG, HEMA, PHEMA, EGDMA, TEGDMA-cross linked polymers, Acrylamide/acrylic polymers, Chitosan, Heprin, etc.

Of interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof.

Polysaccharides useful as a matrix include calcium alginate, and functionalized celluloses, particularly carboxymethylcellulose esters characterized by being water insoluble, molecular weight of about 5 kD to 500 kD, etc. Other polymers of interest include polyvinyl alcohol, esters and ethers, which are biocompatible and may be biodegradable or soluble.

Biocompatible, non-biodegradable polymeric compositions are also used as a matrix. Various non-biodegradable polymers which may be employed are described in U.S. Pat. Nos. 4,303,637; 4,304,765; 4,190,642; 4,186,184; 4,057, 619; 4,052,505; 4,281,654; 4,959,217; 4,014,335; 4,668, 506; 4,144,317. The non-biodegradable polymers may be homopolymers, copolymers, straight, branched-chain, or cross-linked derivatives.

Biocompatible, non-biodegradable polymers of particular interest include polycarbamates or polyureas, particularly polyurethanes, polymers which may be cross-linked to produce non-biodegradable polymers such as cross-linked poly (vinyl acetate) and the like. Also of particular interest are ethylene-vinyl ester copolymers having ail ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

Additional naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly (trifluorochloroethylene), chlorinated poly(ethylene), poly (4,4'-isopropylidene diphenylene carbonate), vinylidene chloride-acrylonitrile copolymer, vinyl chloride-diethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly (halo-olefins), poly(vinyls), poly(acrylate), poly (methacrylate), poly(oxides), poly(esters), poly(amides), and poly(carbonates).

Cells. Cells for use in the assays of the invention can be an organism, a tissue sample, including a biopsy sample, etc. The invention is suitable for use with any cell type, including primary cells, biopsy tissue, etc. Cells of interest can be mammalian cells, including without limitation human cells.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. Tumors of interest for analysis include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

As used herein throughout this disclosure, the term "extracellular vesicle" includes the term "exosome" and all other types of extracellular vesicles. In several embodiments, the exosomes are about 15 nm to about 95 nm in diameter, including about 15 nm to about 20 nm, about 20 nm to about 25 nm, about 25 nm to about 30 nm, about 30 nm to about 35 nm, about 35 nm to about 40 nm, about 40 nm to about 50 nm, about 50 nm to about 60 nm$^3$ about 60 nm to about 70 nm, about 70 nm to about 80 nm, about 80 nm to about 90 nm, about 90 nm to about 95 nm and overlapping ranges thereof. In certain embodiments, larger exosomes are obtained are larger in diameter (e.g., those ranging from about 140 to about 210 nm). Exosomes of interest for the methods disclosed herein comprise nucleic acids, e.g. one or both of DNA and RNA, particularly genomic DNA. Alternative nomenclature is also often used to refer to exosomes. Thus, as used herein the term "exosome" shall be given its ordinary meaning and may also include terms including microvesicles, epididimosomes, argosomes, exosome-like vesicles, microparticles, prominonosomes, prostasomes, dexosomes, texosomes, dex, tex, archeosomes and oncosomes.

Exosomes can be present in biological samples as defined herein, and may be isolated from cellular preparations by methods comprising one or more of filtration, centrifugation, antigen-based capture and the like. For example a cell population or biological sample is collected. The population is then subject to one or more rounds of centrifugation (in several embodiments ultracentrifugation and/or density centrifugation is employed) in order to separate the exosome fraction from the remainder of the cellular contents and debris from the population of cells. In some embodiments, centrifugation need not be performed to harvest exosomes. In several embodiments, pre-treatment of the cells is used to improve the efficiency of exosome capture. For example, in several embodiments, agents that increase the rate of exosome secretion from cells are used to improve the overall yield of exosomes. In some embodiments, augmentation of exosome secretion is not performed. In some embodiments, size exclusion filtration is used in conjunction with, or in place of centrifugation, in order to collect a particular size (e.g., diameter) of exosome. In several embodiments, filtration need not be used. In still additional embodiments, exosomes (or subpopulations of exosomes are captured by selective identification of unique markers on or in the exosomes (e.g., transmembrane proteins)). In such embodiments, the unique markers can be used to selectively enrich a particular exosome population. In some embodiments, enrichment, selection, or filtration based on a particular marker or characteristic of exosomes is not performed.

EV/EP DNA has been implicated in various disease processes both as a mediator of physiological function and a potential biomarker in liquid biopsy applications. EV DNA fragment lengths vary greatly and are largely dependent on the size of the EV with which they are associated. The DNA can range in size from ~200 bp to >2 million bp. These fragments can be chromosomal in nature. EV DNA can be associated with the outer vesicular membrane surface. EV DNA has been shown to contain disease DNA markers, for example in pleural effusions, or in urine from diseases of the urinary tract, such as kidney disease and bladder cancer.

Cells or EVs may be present in a biological sample. The term "sample" as used herein relates to a material or mixture of materials, typically, although not necessarily, in liquid form, containing one or more analytes of interest. In one embodiment, the term as used in its broadest sense, refers to any material containing cells or EVs isolated from an individual (including without limitation plasma, serum, cerebrospinal fluid, lymph, tears, saliva and tissue sections) or from in vitro cell culture constituents, as well as samples from the environment. In some cases, the sample is derived from a human.

The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen).

A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated (e.g. host cell proteins).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.)

As used herein, the term "portion" when used in reference to an amino acid sequence (as in "a portion of a given amino acid sequence") refers to fragments of that sequence. The fragments may range in size from six amino acids to the entire amino acid sequence minus one amino acid (e.g., 6 amino acids, 10, 20, 30, 40, 75, 200, etc.)

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

The term "analyte," as used herein, generally refers to a substance or one or more constituents thereof that is for identification, such as detection (e.g., detection via sequencing). Examples of analytes include, without limitation, DNA, RNA, a labelling agent, antibody, and protein. An analyte may be a cell or one or more constituents of a cell.

Analytes may be of different types. In some examples, in a plurality of analytes, a given analyte is of a different structural or functional class from other analytes of the plurality. Examples of different types of analytes include DNA and RNA; a nucleic acid molecule and a labelling agent; a transcript and genomic nucleic acid; a plurality of nucleic acid molecules, where each nucleic acid molecule has a different function, such as a different cellular function. A sample may have a plurality of analytes of different types, such as a mixture of DNA and RNA molecules, or a mixture of nucleic acid molecules and labelling agents. In some cases, different types of analytes do not include labelling agents directed to separate cell surface features of a cell.

Methods

Methods are provided for the generation of one or more cells embedded in a functional polymer matrix, herein termed "pearls", for the detection and analysis of structural variations at genomic loci. Target cells (or biological sample) for analysis may be isolated, for example, from a subject of interest (from tissues or fluids) wherein the subject is an individual suspected to be suffering from a condition associated with DNA rearrangements, including but not limited to: cancer, immune modulation, changes to immune memory and/or immune function; and the like.

Cells or EVs are optionally sorted, e.g. by flow cytometry, prior to the analysis. For example, FACS sorting or size-differential sorting, can be used to increase the initial concentration of the cells of interest by at least 1,000, 10,000, 100,000, or more fold, according to one or more markers present on the cell surface, e.g. B220, CD3, CD4, CD8, CD25, CD16, CD19, etc. Such cells are optionally sorted according to the presence and/or absence of cell surface markers particularly markers of a population or subpopulation of interest. Analysis of cell staining can be performed using conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide, ethidium monoazaide (EMA), etc.).

One approach is the use of antibodies as affinity reagents. Conveniently, these antibodies can be conjugated with a label for use in separation. Labels include any labels known in the art including, but not limited to, magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

Antibodies can be added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated is any medium that maintains the viability of the cells. One medium which can be utilized is phosphate buffered saline containing from 0.1 to 0.5% BSA. Various media are commercially available and may be used according to the nature of the cells, including Dulbecco's Modified Eagle Medium (dMEM), Hank's Basic Salt Solution (HESS), Dulbecco's phosphate buffered saline (dPBS), RPMI, Iscove's medium, PBS with 5 mM EDTA, etc., frequently supplemented with fetal calf serum, BSA, HSA, etc. The labeled cells can then be quantitated as to the expression of cell surface markers as previously described.

In some embodiments, the cell sample to be analyzed is a primary sample, which may be freshly isolated, frozen, maintained in appropriate culture medium for short periods of time etc. Various media can be employed to maintain cells. The samples may be obtained by any convenient procedure, such as biopsy, the drawing of blood, venipuncture, or the like. Usually the sample is a heterogeneous mixture of cells, comprising a plurality of distinct cell types, distinct populations, or distinct subpopulations, for example 10, 102, 103, 104, 105, 106,107, 108,109, 1010, 1011, 1012 or more different antigenic specificities. Samples may be obtained prior to or after diagnosis, may be obtained through a course of treatment, and the like.

For isolation of cells from tissue, an appropriate solution can be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

A microfluidics device may used to generate single cells embedded in a functional polymer matrix, i.e. pearls. In some embodiments, single cells are directly injected into pre-formed polymer pearls. The polymer matrix is selected to allow for: buffer exchange; permeability to large molecules, e.g. enzymes and proteins; entrapment of nucleic acids inside the matrix during lysis; and stability over a range of temperatures, including without limitation from about −4° C. to about 65° C. In some embodiments the polymer matrix comprises, without limitation, agarose, hydrogel, or Pluronic polymers at concentrations sufficient to inhibit degradation of DNA by mechanical shearing. In some embodiments the embedded cells are lysed in situ, and the matrix is then dissolved in a chaotropic dense salt solution. The matrix is dissolved by the chaotropic salt at ambient temperature, e.g. from about 10° to about 40° C.

Polymers may be used as a matrix at a concentration sufficient to inhibit degradation of DNA by mechanical shearing, which varies by the specific polymer but is generally from 0.1 to about 10%, e.g. from about 0.1%, about 0.2%, about 0.3%, about 0.5%, about 0.75%, about 1%, about 2%, about 2.5%, about 3%, about 4%, about 5%, up to about 10%, up to about 9%, up to about 8%, up to about 7.5%, up to about 7%, up to about 6%, up to about 5%. Ranges include, for example, from 0.1% to 1%, from 0.5% to 2.5%, from 1% to 5%, from 5% to 10%, and intervening ranges. Preferred polymers are free of nucleases.

Some examples of biodegradable polymers useful in the present invention include: hydroxyaliphatic carboxylic acids, either homo- or copolymers, such as polylactic acid, polyglycolic acid, polylactic glycolic acid; polysaccharides such as cellulose or cellulose derivatives such as ethyl or methyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthalate and calcium alginate, polypropylene, polybutyrates, polycarbonate, acrylate polymers such as polymethacrylates, polyanhydrides, polyvalerates, polycaprolactones such as poly-epsilon-caprolactone, polydimethylsiloxane, polyamides, polyvinylpyrollidone, polyvinylalcohol phthalate, gelatin, agarose, starch, alginate, reversibly cross-linked hydrogels, elastin polypeptides, hyaluronan, PEG, HEMA, PHEMA, EGDMA, TEGDMA-cross linked polymers, Acrylamide/acrylic polymers, Chitosan, Heprin, etc.

Polysaccharides useful as a matrix include calcium alginate, and functionalized celluloses, particularly carboxymethylcellulose esters characterized by being water insoluble, molecular weight of about 5 kD to 500 kD, etc. Other polymers of interest include polyvinyl alcohol, esters and ethers, which are biocompatible and may be biodegradable or soluble.

Biocompatible, non-biodegradable polymeric compositions are also used as a matrix. Various non-biodegradable polymers which may be employed are described in U.S. Pat. Nos. 4,303,637; 4,304,765; 4,190,642; 4,186,184; 4,057,619; 4,052,505; 4,281,654; 4,959,217; 4,014,335; 4,668,506; 4,144,317. The non-biodegradable polymers may be homopolymers, copolymers, straight, branched-chain, or cross-linked derivatives.

Biocompatible, non-biodegradable polymers of particular interest include polycarbamates or polyureas, particularly polyurethanes, polymers which may be cross-linked to produce non-biodegradable polymers such as cross-linked poly (vinyl acetate) and the like. Also of particular interest are ethylene-vinyl ester copolymers having ail ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

Additional naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly (trifluorochloroethylene), chlorinated poly(ethylene), poly (4,4'-isopropylidene diphenylene carbonate), vinylidene chloride-acrylonitrile copolymer, vinyl chloride-diethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olef ins), poly(vinyl-olefins), poly(styrene), poly (halo-olefins), poly(vinyls), poly(acrylate), poly (methacrylate), poly(oxides), poly(esters), poly(amides), and poly(carbonates).

In some embodiments, polymer pearls are made using a microfluidics platform. In such embodiments, cells, oil (e.g. mineral oil) and polymer can be mixed in a microfluidic chamber to form pearls comprising a single cell. Pearls provide a benefit of allowing processing of cells while keeping nucleic acids trapped within the matrix. "Pearls" find use in analyses requiring intact genomes, intact high-molecular weight library preparation or for the isolation and processing of DNA or RNA.

A microfluidics device may used to generate single cells embedded in a functional polymer matrix, i.e. pearls. In some embodiments, single cells are directly injected into pre-formed polymer pearls. The polymer matrix is selected to allow for: buffer exchange; permeability to large molecules, e.g. enzymes and proteins; entrapment of nucleic acids inside the matrix during lysis; and stability over a range of temperatures, including without limitation from about −4° C. to about 65° C. In some embodiments the polymer matrix comprises, without limitation, agarose, hydrogel, or Pluronic polymers at concentrations sufficient to inhibit degradation of DNA by mechanical shearing. In some embodiments the embedded cells are lysed in situ, and the matrix is then dissolved in a chaotropic dense salt solution. The matrix is dissolved by the chaotropic salt at ambient temperature, e.g. from about 10° to about 40° C.

Microfluidic technologies allow for the manipulation of fluids down to the micron and sometimes nanometer length scale and femto to microliter volumes, see Jammes, F. C., Maerkl, S. J. Microsyst Nanoeng 6, 45 (2020), herein specifically incorporated by reference. For example, "pearls" can be isolated in channels in combination with single cells; or "pearls" can be formed in channels for cell insertion. This allows for volume reduction, laminar flow, parallel flows, and automation of processes. Microfluidics channels can be made out of various materials, including glass, silicon wafers, polydimethylsiloxane (PDMS), polymethylmethacrylate (PMMA), polycarbonate (PC), etc.

Microfluidic devices may use mechanical filters for sorting cell populations based on their physical properties (size, shape, etc.) in a label-free manner, including weir-style filters, pillar arrays to divert a cell's flow path based on its size or trap large cells, etc. Hydrodynamic filtration utilizes laminar flow andchannel geometries for cell filtration. Pinched flow fractionation uses different inlets to pinch the sample flow against the microfluidic wall with another flow. Deterministic lateral displacement (DLD) allows for separation of particles based on their size.

Passive microfluidic devices do not rely on active on-chip control elements for flow handling and regulate flow behavior by their inherent design. Fluids are driven through such chips either by capillarity or by applying a pressure source. Flow rates can be tuned by adjusting the design of the microfluidic chip or by adjusting the pressure source. Microwell and microtrap arrays are common approaches to isolate individual cells.

Active microfluidics includes Microfluidic Large-Scale Integration (mLSI), which may include on-chip valves by stacking microfluidic channels and pressurizing the control channel. In response to the pressure increase, a membrane separating the two channels will deflect and reversibly pinch off the flow channel. By combining multiple valves, functional elements including peristaltic pumps and multiplexers are generated. The use of valves enables precise flow control on-chip. By combining valves in specific manners, highly complex flow paths can be controlled with a relatively small number of control inputs.

Droplet generation frequency can be tuned and can vary from slow dripping to frequencies of several kHz. Those droplets, e.g. water-in-oil droplets, can encapsulate cells or biological materials, and therefore have the potential for high-throughput single-cell studies. Droplet microfluidics can be used to encapsulate cells.

Commercial systems for microfluidics are available in the art, including, without limitation, Mission Bio Tapestri system, Atomica biochips, Fluidigm, Ufluidics devices, etc.

In some embodiments, the polymer pearls comprising one or more cells are washed to remove oils and any other unwanted compounds or contaminants prior to buffer exchange for lysis. The methods may use further processing steps, including but not limited to, exonuclease treatment to digest linear DNA. The pearls may be dissolved using a salt solution to free the nucleic acids.

In some embodiments, chromatinized DNA is fixed to proteins before dissolving the pearls. In some embodiments, non-destructive labeling of genomic DNA prior to analysis using DNA barcodes, fluorophores, or other unique molecular identifiers via crosslinking reagents such as psoralen conjugates. In some embodiments, crosslinkers may be targeted to specific genomic sequences through drug, nucleic-acid, or other moieties that recognize specifically targeted genomic sequences or may be sequence non-specific. In some embodiments, crosslinking may be chemically or physically reversible to avoid interference with subsequent processing for sequencing pipelines. In some embodiments, after lysis, DNA is digested and the remaining RNA is isolated, modified, reverse PCR'ed, or sub-isolated based on structure, sequence, size, or native modifications. In some embodiments, after lysis, nucleic acid polymers are fragmented. In some embodiments, during fragmentation barcodes are inserted. In some embodiments, during fragmentation primers comprising barcodes and sequencing platform adapters are added to the fragmented nucleic acids using a transposase. In some embodiments the bar-coded nucleic acids are used to generate a library.

A chaotropic agent may be used to dissolve the matrix, which disrupts the structure of, and denatures, macromolecules such as proteins and nucleic acids. Chaotropic salts that dissociate in solution exert chaotropic effects by shielding charges and preventing the stabilization of salt bridges. Hydrogen bonding is stronger in non-polar media, so salts, which increase the chemical polarity of the solvent, can also destabilize hydrogen bonding.

Empirical tables such as the Hofmeister series are available that that delineate these ions and rank order them with respect to their effects on nucleic-acid and protein structures, providing guidance for selection of an agent. For example, see Hyde et al. (2017). "General Principles and Strategies for Salting-Out Informed by the Hofmeister Series". Organic Process Research & Development. 21 (9): 1355-1370, herein specifically incorporated by reference. Salts of interest for use in the methods disclosed herein include, without limitation, Rb trichloroacetic acid (TCA), CsTCA, BaTCA, Rb thiocynanate (SCN), CsSCN, etc. and combinations thereof.

Cells may be lysed following the formation of single cell polymer matrixes. Methods of lysis are known in the art, including ionic or non-ionic surfactants, etc. Ionic surfactants may be of anionic type such as sodium dodecyl sulfate, sodium lauryl ether sulfate, and sodium myreth sulfate, or cationic type such as octenidine dihydrochloride, cetrimonium bromide, cetylpyridinium chloride, benzalkonium chloride, benzethonium chloride, dimethyl dioctadecyl ammonium chloride, and dioctadecyl dimethyl ammonium bromide Non-ionic surfactants include the Triton™ family of detergents, e.g. Triton™ X-15; Triton™ X-35; Triton™ X-45; Triton™ X-100; Triton™ X-102; Triton™ X-114; Triton™ X-165, etc. Brij™ detergents are also similar in structure to Triton™ X detergents in that they have varying lengths of polyoxyethylene chains attached to a hydrophobic chain. The Tween™ detergents are nondenaturing, nonionic detergents, which are polyoxyethylene sorbitan esters of fatty acids. Tween™ 80 is derived from oleic acid with a 018 chain while Tween™ 20 is derived from lauric acid with a $C_{12}$ chain. The zwitterionic detergent, CHAPS, is a sulfobetaine derivative of cholic acid. This zwitterionic detergent is useful for membrane protein solubilization when protein activity is important. The surfactant is contacted with the cells for a period of time sufficient to lyse the cells.

The nucleic acids may be subjected to digestion with a nuclease, e.g. an exonuclease or endonuclease, that selectively digests residual contaminating nucleic acids. For example, analysis of low-copy circular DNAs presents some challenges, in that host gDNA can be present, adding unwanted contaminating DNA for sequencing and other forms of analysis. Certain exonucleases, e.g. Exonuclease V, degrade both linear ss and dsDNA, while keeping the circular DNA intact. Exonuclease V (RecBCD), Nuclease BAL-3, Thermolabile Exonuclease I, T7 Exonuclease, Nuclease P1, Exonuclease III, Exonuclease T, T5 Exonuclease, or any of their derivatives are of interest for this purpose. Alternatively, DNA-specific or RNA-specific nucleases can be used to reduce the presence of the undesired form.

Amplification refers to the process by which DNA templates are increased in number through multiple rounds of replication. Isolated circular DNA can be amplified in vitro, for example. Conveniently, polymerase chain reaction (PCR) is the method of in vitro amplification, but such is not required, and other methods, such as loop-mediated isothermal amplification (LIA); ligation detection reaction (LDR); ligase chain reaction (LCR); nucleic acid sequence based amplification (NASBA); multiple displacement amplification (MDA); C-probes in combination with rolling circle amplification; and the like may find use. See, for example, Kozlowski et al. (2008) Electrophoresis. 29(23):4627-36; Monis et al. (2006) Infect Genet Evol. 6(1):2-12; Zhang et al. (2006) Clin Chim Acta. 363(1-2):61-70; Cao (2004) Trends Biotechnol. 22(1):38-44; Schweitzer and Kingsmore (2001) Curr Opin Biotechnol. 12(1):21-7; Lisby (1999) Mol Biotechnol. 12(1):75-99. As known in the art, amplification reactions can be performed in a number of configurations, e.g. liquid phase, solid phase, emulsion, gel format, etc.

It is preferable to utilize a high fidelity polymerase in the amplification reaction to preserve sequence fidelity, typically a polymerase having an intact proof-reading function, e.g. Pfx50.TM. DNA Polymerase; Pfu polymerase, Vent polymerase, Phusion High-Fidelity DNA Polymerase; and the like.

Primers may comprise nucleotides useful in subsequent sequencing. Such sequences are readily designed by commercially available software programs or companies (e.g. see Biotage). Amplification primers may optionally include a barcode sequence, to aid in the identification of clones (see Parameswaran et al. (2007) Nucleic Acids Research 35(19): e30, herein specifically incorporated by reference).

Custom primers may be utilized, where the primers comprise one or more chemical modifications that increase the melting temperature of the duplex formed between the target DNA and the primer. The modifications may include, without limitation, inclusion of modified nucleotides such as Pyrene, Trimethoxystilbene, 2-Amino-deoxyadenosine, 5-Methyl-deoxycytidine, LNA, BNA, Aminoethyl-phenoxazine-deoxycytidine, C-5 Propynyl-deoxyuridine, C-5 Propynyl-deoxycytidine, MGB, etc. Adding modifications can increase sequencing efficiency, allowing the generated libraries to be sequenced by a sequencing platform of interest. In some embodiments, sequencing efficiency and quality are increase by at least 10% using primer modifications. In some embodiments, sequencing efficiency is increased from 10-20%, 20-30%, 30-40%, 40-50% or >50% using primer modifications.

The term "barcode," as used herein, generally refers to a label, or identifier, that can be part of an analyte to convey information about the analyte. A barcode can be a tag attached to an analyte (e.g., nucleic acid molecule) or a combination of the tag in addition to an endogenous characteristic of the analyte (e.g., size of the analyte or end sequence(s)). The barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample and can be included in a primer or separately added. Barcodes can allow for identification and/or quantification of individual sequencing-reads in real time.

The nucleic acids may be modified with a genome editing platform, e.g. to add barcodes, adaptor sequences, and the like. In some embodiments the genome editing platform comprises the use of transposase-based methods, or "tagmentation," in which a hyperactive transposase is used to simultaneously fragment target DNA and append universal adapter sequences. Tagmentation effectively replaced a series of processing steps in traditional workflows with one single reaction.

Transposases exist in both prokaryotes and eukaryotes and catalyze the movement of defined DNA elements (transposon) to another part of the genome in a 'cut and paste' mechanism. Taking advantage of this catalytic activity, transposases are widely used in many editing applications: for instance, an engineered, hyperactive Tn5 transposase from *E. coli* can bind to synthetic 19 bp mosaic end-recognition sequences appended to Illumina sequencing adapters (termed 'Tn5 transposome') and has been utilized in an in vitro double-stranded DNA (dsDNA) tagmentation reaction (namely simultaneously fragment and tag a target sequence with sequencing adaptors) to achieve rapid and low-input library construction for next-generation sequencing. Transposases of interest for tagmentation include, for example, Tn5, Tn3, Tn7, Tn10, Mu, Mariner, SB, RAG, or variants thereof.

Samples may be sequenced by any convenient method, e.g. by Next Generation Sequencing (NGS), which is a powerful platform that has enabled the sequencing of thousands to millions of DNA molecules simultaneously. A variety of technologies are known and used in the art. In pyrosequencing, the sequencing reaction is monitored through the release of the pyrophosphate during nucleotide incorporation. Sequencing by synthesis utilizes the step-by-step incorporation of reversibly fluorescent and terminated nucleotides for DNA sequencing and is used by the Illumina NGS platforms. Sequencing by ligation relies on short oligonucleotide probes that are ligated to one another. The sequencing reaction commences by binding of the primer to the adapter sequence and then hybridization of the appropriate probe. Ion semiconductor sequencing utilizes the release of hydrogen ions during the sequencing reaction to detect the sequence of a cluster. Each cluster is located directly above a semiconductor transistor which is capable of detecting changes in the pH of the solution. During nucleotide incorporation, a single H+ is released into the solution and it is detected by the semiconductor.

Sequencing platforms include, but are not limited to those commercialized by: Oxford Nanopore, Illumina, 454/Roche Lifesciences including but not limited to the methods and apparatus described in Margulies et al., Nature (2005) 437: 376-380 (2005); and U.S. Pat. Nos. 7,244,559; 7,335,762; 7,211,390; 7,244,567; 7,264,929; 7,323,305; Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; Applied Biosystems (e.g. SOLiD sequencing); Dover Systems (e.g., Polonator G. 007 sequencing); Illumina as described U.S. Pat. Nos. 5,750,341; 6,306,597; and 5,969,119; and Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

For example, CNN-seq is a sequencing approach that incorporates special unique sequence identifiers ("barcodes") at the ends of DNA molecules during library preparation in a way that is fully compatible with on-chip or single molecule sequencing. The CNN-seq barcodes serve as a control for false-positive signals of DNA rearrangement in a way that allows them to be filtered out using standard bioinformatic approaches and custom algorithms that have been developed for such data analysis.

Also provided are reagents and kits thereof for practicing one or more of the above-described methods. The subject reagents and kits thereof may vary greatly. Reagents of interest include reagents specifically designed for use in production of the above described analysis. Kits may include amplification primers, including without limitation one or more of the sets of primers identified herein, reagents amplification and sequence, and such containers as are required for sample collection.

The kits may further include a software package for statistical analysis of the sequences. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Experimental

Complete, accurate, and precise understanding of an organism's complete set of genetic instructions requires three types of information: sequence, structure, and copy number of all of its DNA elements. There is a substantial need for high resolution tools to characterize DNA populations in both healthy and diseased backgrounds, e.g. genomic DNA, eccDNA, genomic DNA fragments present in EVs, and the like.

Tools are provided to dissect the mechanistic requirements for eccDNA formation, and for structural variation in genomic DNA, connecting genomic structural variants to the molecular etiology of rearrangement-dependent diseases, and applying these tools in cellular and animal models.

Genomic systems and microfluidic platforms are engineered to dynamically track genomic rearrangements and specific biomarkers associated with normal (and abnormal) cellular states. This project is built on a multidimensional approach involving molecular and single-cell methods combined with in-vivo studies and computational tools.

The mechanisms and consequences of genomic heterogeneity in cancer and its role in chemotherapeutic-drug resistance are identified. This will foster the development of novel engineering approaches to one of the most-important challenges in cancer treatment.

Novel capture protocols are provided to robustly characterize programmed cellular heterogeneity and its role cellular decision-making and self-nonself interactions. This technology enables the analysis of human clinical samples to investigate how a patient's unique immune signature contributes to progression and outcome of disease.

CNN-seq is a new sequencing approach that incorporates special unique sequence identifiers ("barcodes") at the ends of DNA molecules during library preparation in a way that is fully compatible with on-chip or single molecule sequencing. The CNN-seq barcodes serve as a control for false-positive signals of DNA rearrangement in a way that allows them to be filtered out using standard bioinformatic approaches and custom algorithms that have been developed for such data analysis.

Defining the mechanisms responsible for cellular heterogeneity and functional biodiversity will require engineering of novel high-spatial-resolution (including single-cell) genomics technologies.

A central challenge of biology is to understand how individual cells process information and respond to perturbations. Much of our current knowledge is based on ensemble measurements. However, the average behavior of a population of cells may not be representative of the behavior of any individual cell in the ensemble. Although large ensemble experiments can provide a useful picture of some biological processes, they are ineffective in studying programmed functional diversification processes in multicellular organisms. These processes are integral to cellular communication, development, differentiation, adaptation, decision making, and overall fitness.

Using a microfluidic platform, cell-encapsidating "pearls" are generated, where sorted or purified single cells or groups of cells are embedded in a functionalized polymer matrix. This matrix allows for: 1. Easy buffer exchange (as opposed to double emulsion technologies) 2. Permeability to various enzymes and proteins 3. Entrapment of nucleic acids inside the matrix upon lysis 4. Stability in a wide range of temperatures ($3°$ C.$<T<55°$ C.), which are compatible with various biochemical processes 5. Isolation of RNA and intact high-molecular-weight DNA (sequence, structure, and topology) library preparation. This method is referred to herein as "Boba-seq".

For some embodiments, custom-made sequencing and index primers are used to enhance sequencing efficiency.

Modifications can be made to internally to increase the melting temperature of DNA duplexes. Melting temperature can be increased from 1 to 30° C. where in some embodiments the melting temperature is increased by 1-5° C., 5-10° C., 10-15° C., 15-20° C., 20-25° C. or 25-30° C. Chemical modifications made to primers, include but aren't limited to, Pyrene, Trimethoxystilbene, 2-Amino-deoxyadenosine, 5-Methyl-deoxycytidine, LNA, BNA, Aminoethyl-phenoxazine-deoxycytidine, C-5 Propynyl-deoxyuridine, C-5 Propynyl-deoxycytidine, or MGBs.

Figure 2:
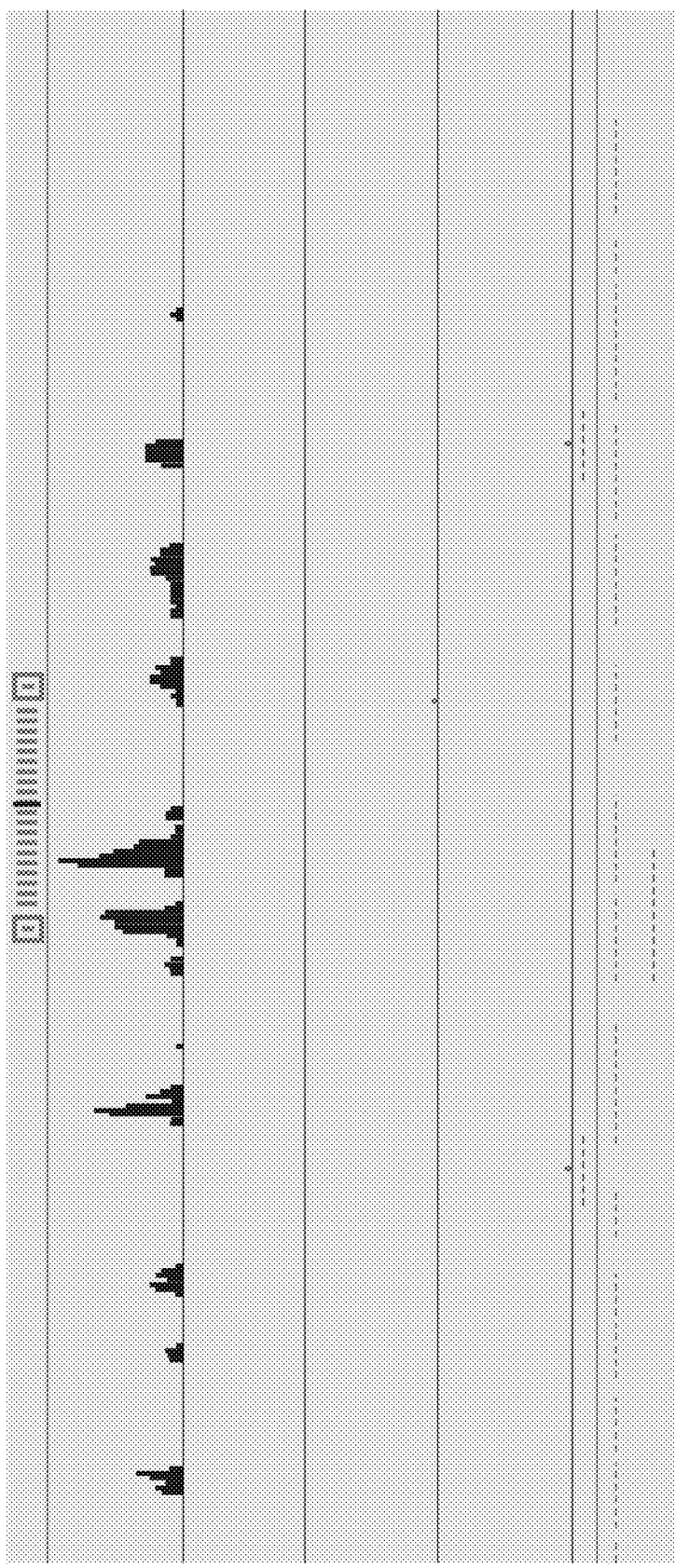
FIG. 2. Isolated eccDNAs were sequenced and mapped to a reference genome for *C. elegans*. Tracks in the top row show the circles isolated using "Boba-seq". This method identified a region of eccDNA that other approaches failed at isolating.

To demonstrate the utility of the polymer-encapsidation and analytical tools disclosed herein, we applied the methodology to analysis of topological genomic rearrangement in groups of cells from *C. elegans* to identify novel regions in eccDNA (FIG. 2) and from groups of human cardiomyocytes to identify deletion junctions (FIG. 3).

Materials and Methods

Generations of cell-containing polymer "pearls". Cells or EVs are added to a microfluidic platform with channels that are specific in size to account for a target number of cells (one or more) per "pearl". One or more cells is combined with hydrogel and oil to form a pearl which is collected, separated, and stored. In some embodiments single cells may be injected directly into pre-formed pearls. When pearls are made using oil, the pearls are washed following formation with to remove oil prior to processing.

Cell processing and transposase complex preparation. In order to lyse cells, pearls were incubated in 0.5% SDS and 2 mg/mL proteinase K at 52° C. for <2 h. Following lysis, pearls were washed x times in TE buffer (10 mM Tris-Cl, 1 mM Na2EDTA pH 8.0). The methods may use the exonuclease ExoV to digest non-circularized to enrich for circular DNAs. DNA from any source, for example isolated nuclei, cells, soft or solid tissues, whole animals, fluids—urine, blood, plasma, saliva, semen, tears, menstrual blood etc. can be processed in this way.

Oligos containing sequence platform adapters and barcodes were annealed together by incubating them in TE buffer in a water bath starting with 85° C. to 23° C. gradually overnight. The number of oligo mixtures made is dependent on the number of samples to be analyzed. Each oligo mixture should contain a unique barcode so that each samples analyzed can be identified. Annealed oligos are then incubated with the transposase protein in 0.1 M Tris-HCL, 0.01 M EDTA and 0.1M NaCl at 23° C. for 30 minutes to form transposase-oligo complexes. This protein DNA complex can be stored at −20° C. in 40% glycerol for one month.

DNA fragmentation and library preparation. Genomic or cDNA in pearls or in (50 mM TAPs, 25 mM MgCl$_2$, pH=8.5) was mixed with 5-50 mg/mL of transposase-oligo. Reaction mixtures were incubated at 37° C. for 25-60 minutes, depending on the size of the library preparation. The reaction is ended with the addition of 0.01% SDS (final concentration). Libraries were generated by mixing DNA from all reaction mixtures in equimolar ratios and applying ~9-22 cycles of PCR to the reaction mixture. PCR was performed using illumina index primers kit in 1X NEBNext (NEB) PCR mix.

Barcode design. Barcodes are inserted between two sequences where the first sequence (black) is the sequencing platform adaptor followed by the barcode (XXXX) ending in the transposase binding sequence. An example is shown below.

```
                                                    SEQ ID NO: 1
          TCGTCGGCAGCGTCXXXXAGATGTGTATAAGAGACAG
```

The length of the barcode sequence is dependent on the number of desired unique combinations. The barcode sequences are chosen to optimize bioinformatic identification.

DNA sequencing. Custom-made sequencing and index primers can be used to enhance sequencing efficiency (and quality of the sequencing reads) for the sequencing platform of interest. For example, modified oligos were used for Illumina on-chip sequencing platform. Primer were made with chemical modifications wherein the modifications were LNAs or Pyrenes and the primer sequences included:

```
                                                    SEQ ID NO: 2
                    TCGTCGGCAGCGTC
                    or
                                                    SEQ ID NO: 3
                    GTCTCGTGGGCTCGG.
```

What is claimed is:

1. A method for analysis of structural variation within genomes; the method comprising:
   isolating one or more cells, purified nuclei, or extracellular vesicles comprising nucleic acids from a biological sample;
   providing a preformed polymer matrix;
   embedding the one or more cells, purified nuclei, or extracellular vesicles comprising nucleic acids into the preformed polymer matrix to form individual pearls containing the one or more cells, purified nuclei, or extracellular vesicles;
   lysing the one or more cells, purified nuclei, or extracellular vesicles in each of the pearls;
   dissolving the polymer matrix of each pearl in a chaotropic dense salt solution;
   fragmenting nucleic acids from the one or more cells, purified nuclei, or extracellular vesicles using a transposase;
   adding barcodes and sequencing platform adaptors to the fragmented nucleic acids to obtain tagged nucleic acid fragments; and
   sequencing the tagged nucleic acid fragments using modified sequencing primers.

2. The method of claim 1, where nucleic acids are cross-linked prior to lysis.

3. The method of claim 1, comprising non-destructive labeling of genomic DNA prior to analysis.

4. The method of claim 3 where the non-destructive labeling of genomic DNA prior to analysis is performed with a crosslinking reagent.

5. The method of claim 3 wherein the non-destructive labeling of genomic DNA prior to analysis is performed with a crosslinking reagent that generates chemically or physically reversible crosslinks.

6. The method of claim 1, wherein the sequencing is performed with a high throughput platform.

7. The method of claim 1 wherein the step of embedding the one or more cells, purified nuclei, or extracellular vesicles comprising nucleic acids into the preformed polymer matrix to form individual pearls comprises;
   mixing cells, oil and preformed polymer matrix in a microfluidic chamber.

8. The method of claim 1, further comprising a step wherein the nucleic acids in pearls are subjected to digestion with an exonuclease or an endonuclease to digest a portion of the nucleic acids.

9. The method of claim 8 wherein the exonuclease is selected from the group consisting of Exonuclease V (RecBCD), Nuclease BAL-3, Thermolabile Exonuclease I, T7 Exonuclease, Nuclease P1, Exonuclease III, Exonuclease T, and T5 Exonuclease.

10. The method of claim 8 wherein the nucleic acids not digested with the exonuclease or endonuclease are circular DNA.

11. The method of claim 8 wherein the nucleic acids not digested with the exonuclease or endonuclease are RNA.

12. The method of claim 1, wherein the nucleic acids in the transposase is selected from the group consisting of Tn5, Tn3, Tn7, Tn10, Mu, Mariner, SB, and RAG.

13. The method of claim 1, wherein sequencing and index primers are used with a sequencing platform of interest.

14. The method of claim 13 wherein the index primers have modifications selected from introduction of Pyrene, Trimethoxystilbene, 2-Amino-deoxyadenosine, 5-Methyl-deoxycytidine, LNA, BNA, Aminoethyl-phenoxazine-deoxycytidine, C-5 Propynyl-deoxyuridine, C-5 Propynyl-deoxycytidine, or MGBs that increase melting temperature of the index primers compared to the index primers without the modifications.

15. The method of claim 1, wherein the fragmented nucleic acids are obtained from circular nucleic acids.

16. The method of claim 15, further comprising isolating the circular nucleic acids prior to the fragmenting of the circular nucleic acids.

17. The method of claim 8, wherein a portion of non-digested nucleic acids are circular nucleic acids.

18. The method of claim 1, wherein the one or more cells, purified nuclei, or extracellular vesicles comprising nucleic acids are injected into the preformed polymer matrix.

19. The method of claim 3, wherein the non-destructive labeling of genomic DNA prior to analysis comprises a step of labeling the genomic DNA with a polynucleotide barcode.

20. The method of claim 3, wherein the non-destructive labeling of genomic DNA prior to analysis comprises a step of labeling the genomic DNA with a fluorophore.

* * * * *

SEQUENCE LISTING

```
Sequence total quantity: 3
SEQ ID NO: 1          moltype = DNA  length = 37
FEATURE               Location/Qualifiers
source                1..37
                      mol_type = other DNA
                      organism = synthetic construct
SEQUENCE: 1
tcgtcggcag cgtcnnnnag atgtgtataa gagacag                          37

SEQ ID NO: 2          moltype = DNA  length = 14
FEATURE               Location/Qualifiers
source                1..14
                      mol_type = other DNA
                      organism = synthetic construct
SEQUENCE: 2
tcgtcggcag cgtc                                                   14

SEQ ID NO: 3          moltype = DNA  length = 15
FEATURE               Location/Qualifiers
```

```
source          1..15
                mol_type = other DNA
                organism = synthetic construct
SEQUENCE: 3
gtctcgtggg ctcgg                                                      15
```